(12) United States Patent
Oshita et al.

(10) Patent No.: US 10,462,892 B2
(45) Date of Patent: Oct. 29, 2019

(54) MEDICAL THERAPEUTIC APPARATUS, METHOD OF USING MEDICAL THERAPEUTIC APPARATUS, AND METHOD OF APPLYING REACTIVE GAS

(71) Applicant: SEKISUI CHEMICAL CO., LTD., Osaka (JP)

(72) Inventors: Takaya Oshita, Nagareyama (JP); Tsuyoshi Uehara, Nara (JP); Yu Nagahara, Kyoto (JP); Yoshishige Takikawa, Osaka (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/333,462

(22) PCT Filed: Jun. 15, 2018

(86) PCT No.: PCT/JP2018/022850
§ 371 (c)(1),
(2) Date: Mar. 14, 2019

(87) PCT Pub. No.: WO2018/230689
PCT Pub. Date: Dec. 20, 2018

(65) Prior Publication Data
US 2019/0215941 A1    Jul. 11, 2019

(30) Foreign Application Priority Data

Jun. 16, 2017 (JP) ................. 2017-119152

(51) Int. Cl.
*H05B 31/26* (2006.01)
*H05H 1/46* (2006.01)
(Continued)

(52) U.S. Cl.
CPC ............. *H05H 1/46* (2013.01); *A61B 18/042* (2013.01); *A61L 2/14* (2013.01); *A61C 17/022* (2013.01); *B01J 19/087* (2013.01)

(58) Field of Classification Search
CPC ....... H05H 1/46; H05H 1/24; H01J 37/32082; H01J 37/32192; H01J 37/32174;
(Continued)

(56) References Cited

U.S. PATENT DOCUMENTS

2015/0010430 A1* 1/2015 Kitano ................. A61L 2/14
422/22

FOREIGN PATENT DOCUMENTS

JP      2012-520101      9/2012
JP      5441066          3/2014
(Continued)

OTHER PUBLICATIONS

International Search Report dated Aug. 14, 2018 in International (PCT) Application No. PCT/JP2018/022850.
(Continued)

*Primary Examiner* — Minh D A
(74) *Attorney, Agent, or Firm* — Wenderoth, Lind & Ponack, L.L.P.

(57) ABSTRACT

The present invention discloses a medical therapeutic apparatus (100) which generates plasma and blows out an reactive gas generated by the generated plasma toward a target object from an outlet, wherein a temperature of the reactive gas at a target surface positioned at a distance of 1 mm or more and 10 mm or less from the outlet is 40° C. or less, and a radical concentration is 0.1 to 300 μmol/L as determined by a hydroxy radical concentration measuring method comprising applying the reactive gas to 0.4 mL of a 0.2 mol/L solution of DMPO (5,5-dimethyl-1-pyrroline-N-oxide) for 30 seconds with a distance from the outlet to a
(Continued)

liquid surface of the solution being 5.0 mm, and measuring a hydroxyl radical concentration of the resulting solution by electron spin resonance (ESR) method.

8 Claims, 7 Drawing Sheets

(51) Int. Cl.
    *A61L 2/14*     (2006.01)
    *A61B 18/04*     (2006.01)
    *A61C 17/022*     (2006.01)
    *B01J 19/08*     (2006.01)

(58) Field of Classification Search
    CPC ...... H01J 37/32623; H01J 41/04; H01J 41/14; H01J 41/06; B82Y 10/00; H01T 23/00; H01T 19/00
    See application file for complete search history.

(56) References Cited

FOREIGN PATENT DOCUMENTS

| | | |
|---|---|---|
| JP | 2017-50267 | 3/2017 |
| WO | 2010/103262 | 9/2010 |
| WO | 2011/027542 | 3/2011 |
| WO | 2013/105659 | 7/2013 |

OTHER PUBLICATIONS

Takamatsu et al., "Investigation of reactive species using various gas plasmas", RSC Advances, vol. 4, 2014, pp. 39901-39905.
Notice of Reasons for Rejection dated Aug. 20, 2019 in Japanese Patent Application No. 2019-525554, with English translation.

\* cited by examiner

MEDICAL THERAPEUTIC APPARATUS, METHOD OF USING MEDICAL THERAPEUTIC APPARATUS, AND METHOD OF APPLYING REACTIVE GAS

TECHNICAL FIELD

The present invention relates to a medical therapeutic apparatus, a method of using the medical therapeutic apparatus, and a method of applying a reactive gas.

Priority is claimed on Japanese Patent Application No. 2017-119152, filed Jun. 16, 2017, the contents of which are incorporated herein by reference.

BACKGROUND ART

Conventionally, apparatuses for medical use such as dental treatment are known, which apply plasma to an affected part of a patient for healing wounds and the like.

For example, Patent Document 1 discloses a dental diagnosis apparatus in which a plasma jet application means is mounted on an instrument for performing dental treatment so as to enable plasma jet application to an affected part.

According to the invention described in Patent Document 1, the generated plasma is directly applied to the affected part in an attempt to heal the wound and the like.

PRIOR ART REFERENCES

Patent Document

Patent Document 1: Japanese Patent Granted Publication No. 5441066

DISCLOSURE OF INVENTION

Problems to be Solved by the Invention

As plasma application apparatuses, there are a plasma jet application apparatus and a reactive gas application apparatus.

The plasma jet application apparatus generates plasma and directly applies the generated plasma together with reactive species to a target object, in which the reactive species are generated by reaction within the plasma or reaction of the plasma with ambient gas, and include reactive oxygen species such as hydroxyl radical, singlet oxygen, ozone, hydrogen peroxide and superoxide anion radical, and reactive nitrogen species such as nitric oxide, nitrogen dioxide, peroxynitrite and dinitrogen trioxide.

The reactive gas application apparatus generates plasma and applies a reactive gas to a target object, in which the reactive gas contains reactive species generated by reaction within the plasma or reaction of the plasma with ambient gas or moisture contained in the target object. Examples of the reactive species include reactive oxygen species such as hydroxyl radical, singlet oxygen, ozone, hydrogen peroxide and superoxide anion radical, and reactive nitrogen species such as nitric oxide, nitrogen dioxide, peroxynitrite and dinitrogen trioxide.

The composition of the reactive gas varies depending on the plasma generating gas and the ambient gas.

Further, the effects of plasma application vary depending on the composition of the reactive gas.

However, in a plasma jet application apparatus for generating low temperature plasma used in medical applications, the plasma generating gas for generating plasma is generally limited to noble gas.

Accordingly, an object of the present invention is to provide a medical therapeutic apparatus capable of generating plasma using a wide variety of plasma generating gas and applying the resulting reactive gas to a target object.

Means to Solve the Problems

[1] A medical therapeutic apparatus which generates plasma and blows out a reactive gas generated by the generated plasma toward a target object from an outlet, wherein a temperature of the reactive gas at a target surface positioned at a distance of 1 mm or more and 10 mm or less from the outlet is 40° C. or less, and a radical concentration is 0.1 to 300 µmol/L as determined by a hydroxy radical concentration measuring method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method.

[2] A medical therapeutic apparatus which generates plasma and blows out a reactive gas generated by the generated plasma toward a target object from an outlet, wherein a temperature of the reactive gas at a target surface positioned a distance of 1 mm or more and 10 mm or less from the outlet is 40° C. or less, and a singlet oxygen concentration is 0.1 to 300 µmol/L as determined by a singlet oxygen concentration measuring method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[3] A medical therapeutic apparatus which generates plasma and blows out a reactive gas generated by the generated plasma toward a target object from an outlet, wherein a temperature of the reactive gas at a target surface positioned at a distance of 1 mm or more and 10 mm or less from the outlet is 40° C. or less, a hydroxyl radical concentration is 0.1 to 300 µmol/L, and a singlet oxygen concentration is 0.1 to 300 µmol/L, wherein the hydroxy radical concentration is measured by a method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method, and the singlet oxygen concentration is measured by a method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[4] The medical therapeutic apparatus according to any one of [1] to [3], which is for dental use.

[5] A method of using a medical therapeutic apparatus, comprising providing the medical therapeutic apparatus according to any one of [1] to [4], and applying the reactive gas to a target object using the medical therapeutic apparatus.

[6] A method of applying an reactive gas to a target object, excluding medical practice on human body, comprising applying a voltage to a plasma generating gas to generate plasma, and applying an reactive gas generated by the plasma to a target object selected from a cell, a living tissue and a whole body of an organism, to thereby promote cleaning, activation or healing of abnormalities of the target object, wherein a temperature of the reactive gas at a target surface positioned at a distance of 1 mm or more and 10 mm or less from the outlet is 40° C. or less, and a radical concentration is 0.1 to 300 µmol/L as determined by a hydroxy radical concentration measuring method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method.

[7] A method of applying an reactive gas to a target object, excluding medical practice on human body, comprising applying a voltage to a plasma generating gas to generate plasma, and applying an reactive gas generated by the plasma to a target object selected from a cell, a living tissue and a whole body of an organism, to thereby promote cleaning, activation or healing of abnormalities of the target object, wherein a temperature of the reactive gas at a target surface at a distance of 1 mm or more and 10 mm or less from the outlet is 40° C. or less, and a singlet oxygen concentration is 0.1 to 300 µmol/L as determined by a singlet oxygen concentration measuring method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[8] A method of applying an reactive gas to a target object, excluding medical practice on human body, comprising applying a voltage to a plasma generating gas to generate plasma, and applying an reactive gas generated by the plasma to a target object selected from a cell, a living tissue and a whole body of an organism, to thereby promote cleaning, activation or healing of abnormalities of the target object, wherein a temperature of the reactive gas at a target surface positioned at a distance of 1 mm or more and 10 mm or less from the outlet is 40° C. or less, a hydroxyl radical concentration is 0.1 to 300 µmol/L, and a singlet oxygen concentration is 0.1 to 300 µmol/L, wherein the hydroxy radical concentration is measured by a method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method, and the singlet oxygen concentration is measured by a method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[9] The method according to any one of [6] to [8], wherein the plasma generating gas contains nitrogen gas as a main component.

[10] The method according to any one of [6] to [9], wherein the plasma generating gas has an oxygen concentration of 1% by volume or less.

[11] A therapeutic method comprising applying a voltage to a plasma generating gas to generate plasma, and applying an reactive gas generated by the plasma to a target object selected from a cell, a living tissue and a whole body of a human, wherein a temperature of the reactive gas at a target surface positioned at a distance of 1 mm or more and 10 mm or less from an outlet for the reactive gas is 40° C. or less, and a hydroxyl radical concentration is 0.1 to 300 µmol/L as determined by a hydroxy radical concentration measuring method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method.

[12] A therapeutic method comprising applying a voltage to a plasma generating gas to generate plasma, and applying an reactive gas generated by the plasma to a target object selected from a cell, a living tissue and a whole body of a human, wherein a temperature of the reactive gas at a target surface positioned a distance of 1 mm or more and 10 mm or less from an outlet for the reactive gas is 40° C. or less, and a singlet oxygen concentration is 0.1 to 300 µmol/L as determined by a singlet oxygen concentration measuring method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[13] A therapeutic method comprising applying a voltage to a plasma generating gas to generate plasma, and applying an reactive gas generated by the plasma to a target object selected from a cell, a living tissue and a whole body of a human, wherein a temperature of the reactive gas at a target surface positioned at a distance of 1 mm or more and 10 mm or less from an outlet for the reactive gas is 40° C. or less, a hydroxyl radical concentration is 0.1 to 300 µmol/L, and a singlet oxygen concentration is 0.1 to 300 mµmol/L, wherein the hydroxy radical concentration is measured by a method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method, and the singlet oxygen concentration is measured by a method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

[14] The therapeutic method according to any one of [11] to [13], wherein the plasma generating gas contains nitrogen gas as a main component.

[15] The therapeutic method according to any one of [11] to [14], wherein the plasma generating gas has an oxygen concentration of 1% by volume or less.

Effect of the Invention

The medical therapeutic apparatus of the present invention is capable of generating plasma using a wide variety of plasma generating gas and applying the resulting reactive gas to a target object.

DESCRIPTION OF THE EMBODIMENTS

The medical therapeutic apparatus of the present invention generates plasma and blows out a reactive gas generated by the generated plasma toward a target object from an outlet.

In the present specification, the reactive gas refers to a gas having high chemical activity and including any of reactive species such as radicals, excited atoms, excited molecules, ions, and the like.

Hereinbelow, the present invention is described based on the preferred embodiments thereof with reference to the drawings.

《Medical Therapeutic Apparatus》

Figure 1:
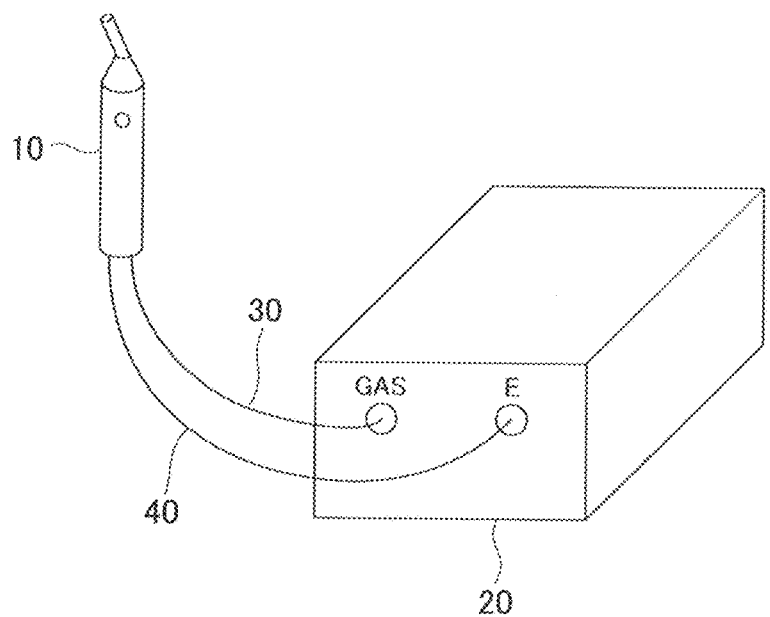
FIG. 1 is a schematic view of a medical therapeutic apparatus according to an embodiment of the present invention.

FIG. 1 shows a schematic view of a medical therapeutic apparatus 100 according to an embodiment of the present invention.

The medical therapeutic apparatus 100 includes an instrument 10, a power supply unit 20, a gas conduit 30, and an electrical wiring 40. The instrument 10 is connected to the power supply unit 20 via the gas conduit 30 and the electrical wiring 40. It is preferable that the gas conduit 30 and the electric wiring 40 are bundled together and connected to the instrument 10.

The instrument 10 is a device that blows out a reactive gas generated by the plasma from an outlet.

Figure 2:
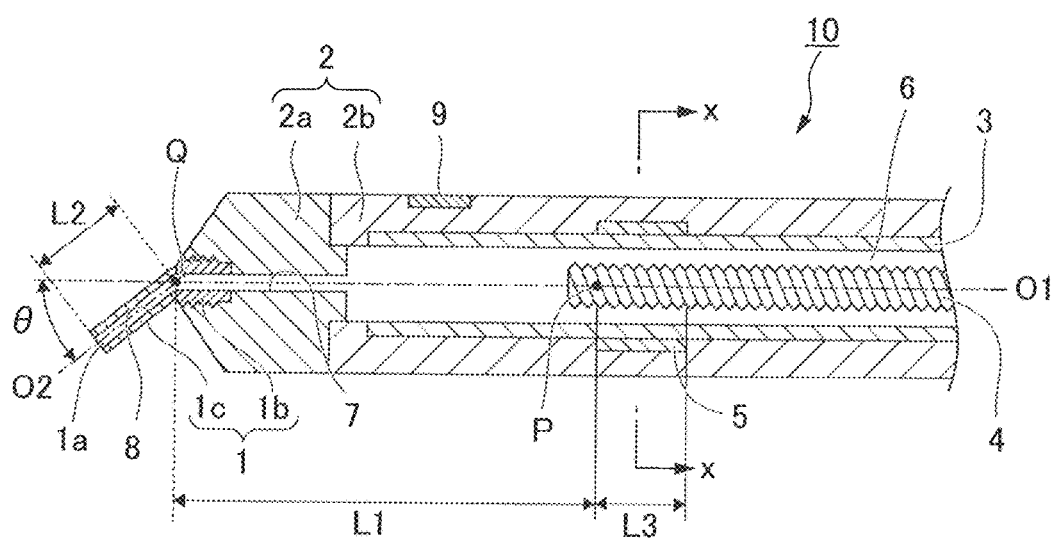
FIG. 2 is a partial cross-sectional view of an instrument used in a medical therapeutic apparatus according to an embodiment of the present invention.

As shown in FIG. 2, the instrument 10 includes a nozzle 1 and a tubular cowling 2. The nozzle 1 includes a base 1b and an outlet tube 1c extending from the base 1b.

The cowling 2 is composed of a head 2a and a body 2b. The shape of a tip end of the head 2a is tapered, and a nozzle 1 is provided on the apex of the head 2a. The base 1b of the nozzle 1 and the head 2a of the cowling 2 are detachably fitted. A switch 9 is provided on the outer surface of the body 2b.

A flow path 7 is formed inside the head 2a of the cowling 2 and the base 1b.

A flow path 8 is formed inside the outlet tube 1c of the nozzle 1. An outlet 1a for blowing out a reactive gas generated by the plasma is formed on the tip end side of the outlet tube 1c.

In the inner space of the cowling 2, a tubular dielectric 3, an inner electrode 4, and an outer electrode 5 are provided. The tubular dielectric 3 is installed so as to extend in the longitudinal direction and is in contact with the inner surface of the cowling 2. The tube axis O1 of the tubular dielectric 3 coincides with the tube axis of the cowling 2. A cylindrical inner electrode 4 is installed in the hollow portion of the tubular dielectric 3. The tube axis of the inner electrode 4 coincides with the tube axis O1 of the tubular dielectric 3. The inner surface of the tubular dielectric 3 and the inner electrode 4 are positioned apart from each other, and the flow path 6 is formed therebetween. The flow path 6 is a flow path through which the plasma generation gas is allowed to flow. The flow paths 6, 7, 8 communicate with each other and extend to the outlet 1a. A tubular outer electrode 5 is disposed on a part of the outer peripheral portion of the tubular dielectric 3 in which the inner electrode 4 is disposed. The tube axis of the outer electrode 5 coincides with the tube axis O1 of the tubular dielectric 3.

Figure 3:
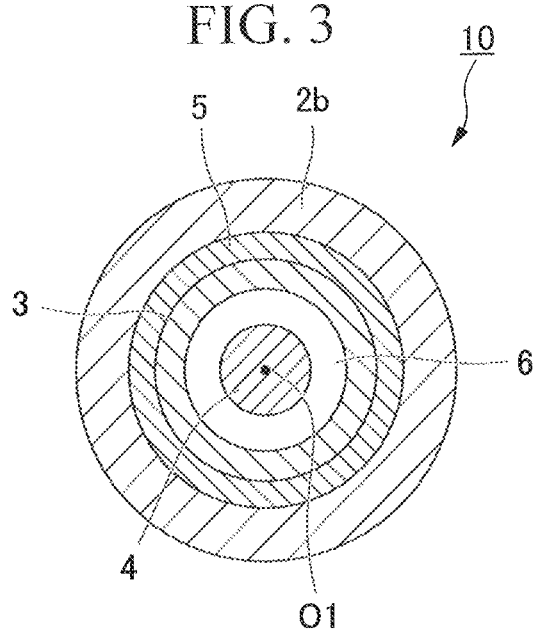
FIG. 3 is a cross-sectional view of the instrument of FIG. 2 as viewed from the arrow direction of the x-x line of FIG. 2.
Figure 4:
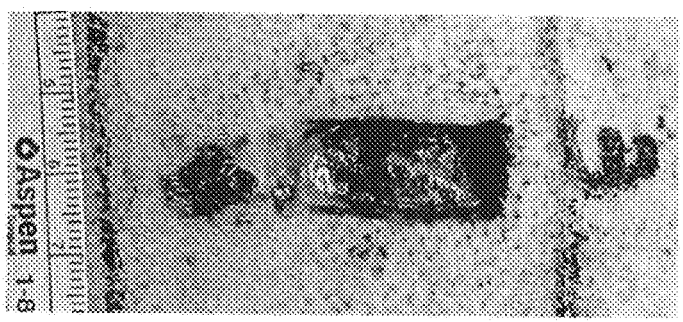
FIG. 4 is a photograph of an initial stage of the wound in Example 7.
Figure 5:
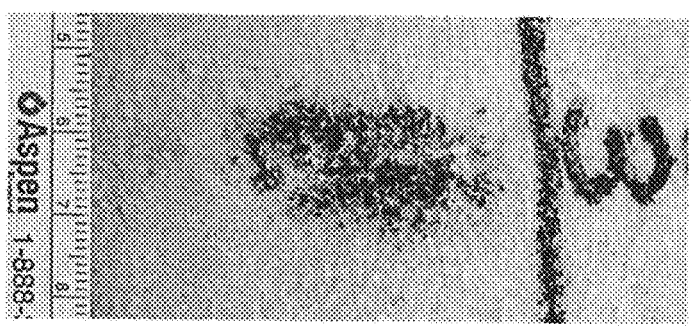
FIG. 5 is a photograph of the wound on day 14 in Example 7.
Figure 6:
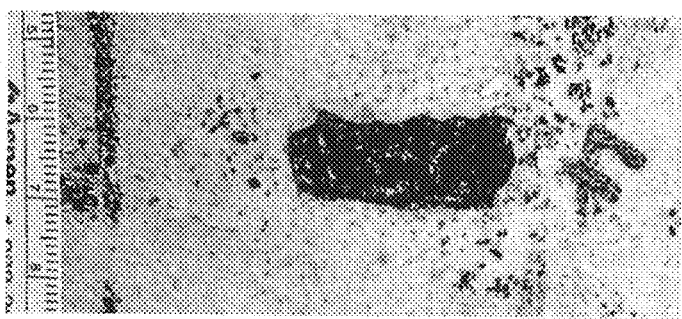
FIG. 6 is a photograph of an initial stage of the wound in Example 8.
Figure 7:
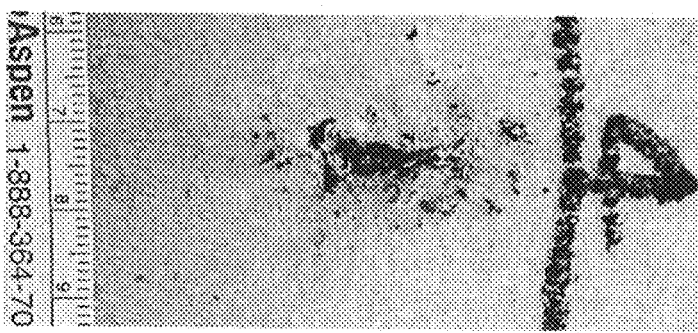
FIG. 7 is a photograph of the wound on day 14 in Example 8.
Figure 8:
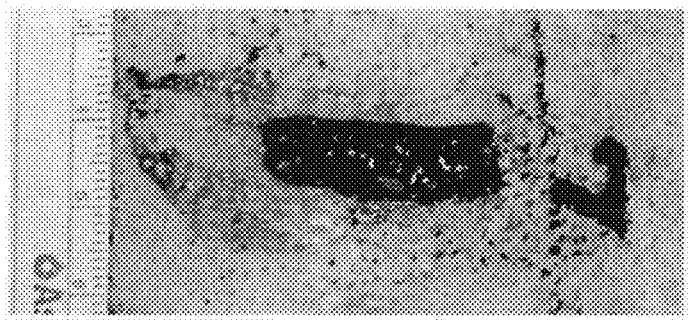
FIG. 8 is a photograph of an initial stage of the wound in Example 13.
Figure 9:
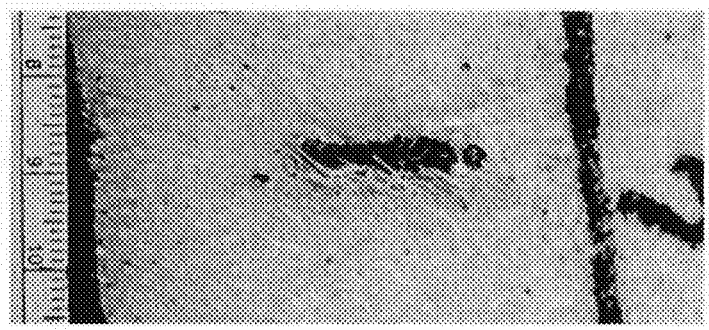
FIG. 9 is a photograph of the wound on day 14 in Example 13.
Figure 10:
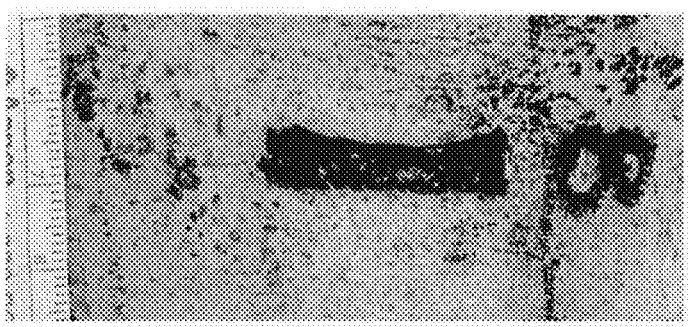
FIG. 10 is a photograph of an initial stage of the wound in Example 14.
Figure 11:
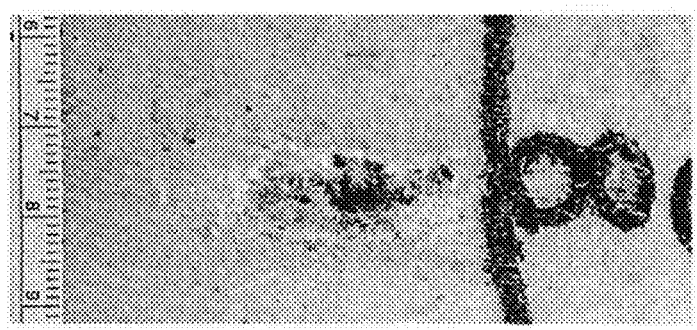
FIG. 11 is a photograph of the wound on day 14 in Example 14.

FIG. 3 shows a cross-sectional view as viewed from the arrow direction of the x-x line of FIG. 2. As shown in FIG. 3, the cylindrical cowling 2, the cylindrical outer electrode 5, the tubular dielectric 3, and the inner electrode 4 form concentric circles and are positioned in this order from the outside to the center (tube axis O1). The outer electrode 5 is disposed in close contact with the outer peripheral surface of the tubular dielectric 3. The outer electrode 5 is disposed in close contact with the inner peripheral surface of the body 2b of the cowling 2.

The inner electrode 4 is disposed at a position including the center of the concentric circles and is arranged to be spaced apart from the inner peripheral surface of the tubular dielectric 3. The flow path 6 is formed between the inner electrode 4 and the tubular dielectric 3, and the plasma generating gas is allowed to flow through the flow path 6.

The tube axis O2 of the nozzle 1 intersects the tube axis O1 of the tubular dielectric 3 at point Q so as to form an angle θ. The angle θ formed by the tube axis O1 and the tube axis O2 can be appropriately set in consideration of the specific use of the medical therapeutic apparatus 100 and the like.

The opening diameter of the outlet 1a is preferably, for example, 0.5 to 5 mm. When the opening diameter is not less than the above lower limit value, the pressure loss of the reactive gas can be suppressed. When the opening diameter is not more than the above upper limit value, the flow velocity of the blown-out reactive gas can be increased to further promote healing and the like.

The length (that is, the distance L2) of the flow path 8 in the outlet tube 1c can be appropriately set in consideration of the use of the medical therapeutic apparatus 100 or the like.

The material of the nozzle 1 is not particularly limited, and may or may not be an insulating material. The material of the nozzle 1 is preferably a material excellent in abrasion resistance and corrosion resistance. As such a material excellent in abrasion resistance and corrosion resistance, a metal such as stainless steel can be mentioned.

The flow path 7 formed in the head 2a of the cowling 2 is on a straight line extension of the tube axis O1. The distance L1 from the tip center point P of the outer electrode 5 to the intersection point Q between the tube axis O1 and the tube axis O2 is set in consideration of the desired size of the medical therapeutic apparatus 100, the temperature of the reactive gas at the gas-applied surface (target surface), and the like.

The shape of the cowling 2 is not particularly limited, but is preferably such that the outer electrode 5 and the inner electrode 4 can be accommodated in the inner space of the cowling 2. It is preferable that the tubular dielectric 3 is also accommodated in the inner space. Although it is preferable that the cowling 2 has a cylindrical shape, the cowling 2 may have a shape designed so as to be easily held by hand.

The sizes of the head 2a of the cowling 2 and the nozzle 1 are preferably such that these can be inserted into a human oral cavity, because the instrument 10 can be easily applied to a dental treatment apparatus.

The body 2b of the cowling 2 is preferably made of an electrically insulating material from the viewpoint of preventing electric shock. For example, the body 2b may be formed of only an electrically insulating material, or may have a multilayer structure having a layer of an electrically insulating material and a layer of a metal material formed on the surface thereof.

Examples of the electrically insulating material include thermoplastic resins such as polyethylene, polypropylene, polyvinyl chloride and polystyrene; and thermosetting resins such as a phenol resin, a melamine resin, a urea resin, an epoxy resin and an unsaturated polyester resin.

Examples of the metal material include stainless steel, titanium, aluminum, and the like.

The material of the head 2a of the cowling 2 is not particularly limited, and a metal material may be used as well as the electrically insulating materials described above. The material of the head 2a is preferably a material excellent in abrasion resistance and corrosion resistance. As such a material excellent in abrasion resistance and corrosion resistance, a metal such as stainless steel can be mentioned. The materials of the head 2a and the body 2b may be the same or different.

The material of the tubular dielectric 3 is not particularly limited, and a dielectric material used for a known plasma generator can be employed. Examples of the material of the tubular dielectric 3 include glass, ceramics, synthetic resins, and the like. The dielectric constant of the tubular dielectric 3 is preferably as low as possible. As the material of the tubular dielectric 3, glass having a low dielectric constant is preferable.

The cross-sectional shape of the tubular dielectric 3 is not particularly limited, and examples thereof include a circle, an ellipse, a square, a hexagon, and the like.

On the outer peripheral surface of the inner electrode 4, a threaded groove(s) (that is, a spiral groove(s)) is provided. That is, a spiral ridge is provided on the outer peripheral surface of the inner electrode 4. In FIG. 2, the outer peripheral surface of the inner electrode 4 faces the inner peripheral surface of the outer electrode 5 with the tubular dielectric 3 interposed therebetween. The screw threads provided on the outer peripheral surface of the inner electrode 4 are positioned in proximity to the inner peripheral surface of the outer electrode 5. The threaded groove(s) (screw groove(s)) provided on the outer peripheral surface of the inner electrode 4 is disposed at a position away from the inner peripheral surface of the outer electrode 5.

With the above arrangement, the electric field at the crest of the screw thread of the inner electrode is locally enhanced and the discharge inception voltage becomes low, so that plasma can be generated and maintained with low electric power.

In the regions where the inner electrode 4 and the outer electrode 5 face each other, the distances between the crest of the screw thread (provided on the outer peripheral surface of the inner electrode 4) and the inner peripheral surface of the outer electrode 5 at different locations may be the same at all of the locations or may be different. It is preferable that the crest of the screw thread is positioned in proximity to the inner peripheral surface of the outer electrode 5 at two or more locations on the screw thread. For example, the distance at which a low temperature plasma can be generated under atmospheric pressure may be 0.01 to 2.0 mm.

The length L3 of the region where the inner electrode 4 faces the outer electrode 5 is preferably 1 to 100 mm, and more preferably 2 to 50 mm. When the length L3 is not less than the above lower limit value, plasma generation sites can be increased to generate plasma more efficiently. When the length L3 is not more than the above upper limit value, the temperature rise of the plasma gas is suppressed, and the temperature of the reactive gas at the target surface can be kept low. In the present embodiment, the length L3 is equal to the length of the outer electrode 5.

The outer electrode 5 may be divided into two or more sections in the direction of tube axis O1. When the outer electrode 5 is divided in the direction of tube axis O1, the length L3 is a length from the rear end to the tip end of the combination of the two outer electrode sections and includes a distance (gap length) between the two outer electrode sections.

The shape of the inner electrode 4 provided in the instrument 10 is not limited to a shape having a threaded groove(s), but may be a shape having irregularities on the electrode surface facing the outer electrode 5. Examples of the shape include a coil shape, and a shape in which a plurality of bumps (protrusions), holes, or through holes are formed on the outer peripheral surface of the rod-shaped or tubular inner electrode 4. The shape of cross-section orthogonal to the tube axis O1 of the inner electrode 4 is not particularly limited, and examples thereof include a circle, an ellipse, a square, a hexagon, and the like.

The material of the inner electrode 4 is not particularly limited as long as the material is electrically conductive, and metals used for electrodes of known plasma generators can be used.

The shape of the outer electrode 5 is not particularly limited as long as it can be disposed along the inner electrode 4, and examples thereof include a cylindrical shape, a rod shape, a plate shape, and the like. The shape of the outer electrode 5 is preferably a cylindrical shape and more preferably a cylindrical shape having such an inner diameter that allows the outer electrode 5 to be placed in close contact with the outer peripheral surface of the tubular dielectric 3. Such a cylindrical shape of the outer electrode 5 enables the outer electrode 5 to be disposed such that the inner peripheral surface of the outer electrode 5 surely faces the outer peripheral surface of the inner electrode 4.

When the outer electrode 5 is in the form of a rod or a plate, the number of the outer electrodes 5 is not particularly limited, and may be one or two or more. When two or more outer electrodes 5 are installed, it is preferable to dispose the outer electrodes 5 at even intervals on the outer periphery of the tubular dielectric 3, because the places for ionizing the plasma generation gas can be dispersed.

The material of the outer electrode 5 is not particularly limited as long as the material is electrically conductive, and metals used for electrodes of known plasma generators can be used. The materials of the outer electrode 5 and the inner electrode 4 may be the same or different.

The power supply unit 20 is a device that supplies electricity to the instrument 10. As the power supply unit 20, a known electric supply device can be used.

The power supply unit 20 preferably has a function of controlling the voltage and the frequency to be applied between the outer electrode 5 and the inner electrode 4.

The power supply unit 20 is a device that transmits electric power to the instrument 10. The power supply unit 20 in the present embodiment is provided with a pump that sends a plasma generating gas to the instrument 10 via the gas conduit 30. The power supply unit 20 can control the voltage and the frequency to be applied between the outer electrode 5 and the inner electrode 4.

The power supply unit 20 may not have a pump. In such case, a pump may be provided independently of the power supply unit 20. Alternatively, the plasma generating gas may also be supplied to the instrument 10 by pressure at the plasma generating gas supply source.

The gas conduit 30 is a path for supplying the plasma generating gas from the power supply unit 20 to the instrument 10. The gas conduit 30 is connected to the rear end of the tubular dielectric 3 of the instrument 10. The material of the gas conduit 30 is not particularly limited, and a material used for known gas pipes can be applied. Concerning a material of the gas conduit 30, for example, a resin pipe, a rubber tube and the like can be used, and a material having flexibility is preferable.

The electrical wiring 40 is a wiring for supplying electricity from the power supply unit 20 to the instrument 10. The electric wiring 40 is connected to the inner electrode 4, the outer electrode 5 and the switch 9 of the instrument 10. The material of the electric wiring 40 is not particularly limited, and a material used for a known electric wiring can be employed. As a material of the electric wiring 40, a metal lead wire covered with an insulating material and the like can be mentioned.

<<How to Use Medical Therapeutic Apparatus>>

A method of using the medical therapeutic apparatus 100 will be described below with reference to FIGS. 1 and 2. The plasma generating gas is supplied from the power supply unit 20 to the instrument 10. The plasma generating gas supplied to the instrument 10 is introduced from the rear end of the tubular dielectric 3 into the hollow portion of the tubular dielectric 3.

Then, electricity is supplied from the power supply unit 20 to the instrument 10, and the switch 9 is turned on to apply a voltage between the inner electrode 4 and the outer electrode 5. The plasma generating gas introduced into the hollow portion of the tubular dielectric 3 is ionized at a position where the inner electrode 4 and the outer electrode 5 face each other.

In the present invention, the inner electrode 4 and the outer electrode 5 face each other in a direction orthogonal to the flowing direction of the plasma generating gas. Accordingly, the plasma generated at the position where the outer peripheral surface of the inner electrode 4 and the inner peripheral surface of the outer electrode 5 face each other is guided to the outlet 1a via the flow paths 6,7 and 8. Plasma is a reactive gas containing ions, electrons, excited molecules and atoms, reactive species depending on the type of plasma generating gas, and the like. As the reactive gas advances further away from the plasma generating unit, the composition of the reactive gas changes, and at the time when the reactive gas reaches the outlet 1a, the ions and the electrons are reunited, while the reactive species become the main constituents of the reactive gas. Further, the gas present in the vicinity of the outlet 1a may react with the ejected reactive gas to generate another kind of reactive gas. As a result, a reactive gas corresponding to the plasma generating gas and the gas present in the vicinity of the outlet 1a is blown out from the outlet 1a.

Therefore, the fluid blown out from the nozzle 1 does not include the plasma itself but is a reactive gas containing reactive species generated by the plasma. In this respect, the medical therapeutic apparatus 100 of the present invention is different from the conventional plasma jet application apparatus.

Examples of the reactive species (radicals etc.) contained in the reactive gas include hydroxyl radicals, singlet oxygen, ozone, hydrogen peroxide, superoxide anion radicals, nitric oxide, nitrogen dioxide, peroxynitrite, dinitrogen trioxide and the like.

The inner electrode 4 and the outer electrode 5 are arranged such that the outer peripheral surface of the inner electrode 4 (disposed in the hollow portion of the tubular dielectric 3) and the inner peripheral surface of the outer electrode 5 face each other through the tubular dielectric 3. The electric field at the tip portion of the screw thread of the inner electrode 4 is locally enhanced and the discharge inception voltage becomes low, so that plasma can be generated and maintained with low electric power.

This effect of generating and maintaining plasma with low electric power can be obtained likewise even when the outer peripheral surface of the inner electrode 4 is not threaded, as long as the inner electrode 4 has a plurality of concavities and convexities formed on its outer peripheral surface as mentioned above.

The inner electrode 4 may not have concavities and convexities such as screw threads on the outer peripheral surface. That is, the inner electrode 4 may be a cylinder without any concavities or convexities on its outer peripheral surface.

The temperature of the reactive gas at a target surface positioned at a distance of 1 mm or more and 10 mm or less from the outlet 1a is 40° C. or less. By setting the temperature of the reactive gas at a target surface to 40° C. or less, stimulus to the target surface can be reduced.

The temperature of the reactive gas at a target surface is a temperature value measured by placing the tip of a rod type thermocouple on the target surface. The temperature of the reactive gas at a target surface can be adjusted by controlling the temperature of the reactive gas at the outlet $1a$ of the nozzle 1 as described later.

The temperature of the reactive gas at the outlet $1a$ of the nozzle 1 is preferably 50° C. or less, more preferably 45° C. or less, and even more preferably 40° C. or less.

When the temperature of the reactive gas at the outlet $1a$ of the nozzle 1 is not more than the upper limit value, the temperature of the reactive gas at the target surface can be easily adjusted to 40° C. or less.

The lower limit value of the temperature of the reactive gas at the outlet $1a$ of the nozzle 1 is not particularly limited, and is, for example, 0° C. or more.

The temperature of the reactive gas blown out from the outlet $1a$ of the nozzle 1 can be adjusted by the flow rate of the plasma generating gas introduced into the tubular dielectric 3, the distance that the plasma travels (the total distance of L1 and L2 shown in FIG. 2) and the plasma gas temperature at the position of plasma generation, some or all which may be controlled in combination.

The flow rate of the plasma generating gas introduced into the tubular dielectric 3 is preferably 1 L/min to 10 L/min.

When the flow rate of the plasma generating gas is not lower than the above lower limit value, the promotion of cleaning, activation or healing of a target object selected from a cell, a living tissue and a whole body of an organism is facilitated. When the flow rate is not more than the above upper limit value, the temperature of the reactive gas at the outlet $1a$ of the nozzle 1 can be easily adjusted to 50° C. or less.

In the medical therapeutic apparatus 100, the ratio of the flow rate (introduction flow rate) of the plasma generating gas introduced into the tubular dielectric 3 and the flow rate (flowout rate) of the reactive gas blown out from the outlet $1a$ (inflow rate:outflow rate) is preferably 0.8 to 1.2, more preferably 0.9 to 1, and still more preferably 1:1. Adjusting the introduction flow rate and the outflow rate so as to fall within the above range enables easy control of the outflow rate. The introduction flow rate and the outflow rate can be adjusted to fall within the above range by appropriately adjusting the shape of the tubular dielectric 3 and the opening diameter of the outlet $1a$.

The temperature of the reactive gas at the outlet $1a$ of the nozzle 1 can be adjusted depending on the total distance of L1 and L2. The total distance of L1 and L2 is appropriately set in consideration of the desired size of the medical therapeutic apparatus 100, the temperature of the reactive gas at the target surface, and the like.

When the total distance of L1 and L2 is long, the reactive gas temperature at the target surface can be lowered. When the total distance of L1 and L2 is short, the radical concentration of the reactive gas can be further increased, and the effects of cleaning, activation, healing, etc. on the target surface can be further enhanced.

The total distance of L1 and L2 can be adjusted depending on the length of the outlet tube $1c$, and the installation positions of the inner electrode 4 and the outer electrode 5.

The temperature of the reactive gas blown out from the outlet $1a$ of the nozzle 1 can be adjusted by the plasma gas temperature at the position of plasma generation.

By lowering the plasma gas temperature at the position of plasma generation, the temperature of the reactive gas blown out from the outlet $1a$ can be lowered. The plasma gas temperature at the position of plasma generation is appropriately set depending on the level and frequency of the voltage applied between the inner electrode 4 and the outer electrode 5.

The radical concentration of the reactive gas generated by the plasma is 0.1 to 300 μmol/L. The radical concentration of the reactive gas generated by the plasma is preferably 0.1 to 100 μmol/L, more preferably 0.1 to 50 μmol/L.

When the radical concentration of the reactive gas generated by the plasma is not lower than the lower limit value, the promotion of cleaning, activation or healing of abnormalities of a target object selected from a cell, a living tissue and a whole body of an organism is facilitated. When the singlet oxygen concentration is not more than the upper limit value, stimulus to the target surface can be easily reduced.

The radical concentration of the reactive gas generated by the plasma can be adjusted by the flow rate of the plasma generating gas introduced into the tubular dielectric 3, the total distance of L1 and L2 and the plasma gas temperature at the position of plasma generation, some or all which may be controlled in combination.

The flow rate of the plasma generating gas introduced into the tubular dielectric 3 is preferably 1 L/min to 10 L/min, more preferably 1 to 5 L/min, still more preferably 1 to 3 L/min.

When the flow rate of the plasma generation gas introduced into the tubular dielectric 3 is not less than the above lower limit value, the radical concentration can be easily adjusted to 0.1 μmol/L or more. When the flow rate is not more than the above upper limit value, the temperature of the reactive gas at the target surface can be easily adjusted to 40° C. or less.

The radical concentration of the reactive gas generated by the plasma can be determined by the following hydroxyl radical concentration measuring method using the medical therapeutic apparatus.

<Hydroxyl Radical Concentration Measuring Method>

A reactive gas is applied to 0.4 mL of a 0.2 mol/L solution of DMPO (5,5-dimethyl-1-pyrroline-N-oxide) for 30 seconds. Here, the distance from the outlet to a liquid surface of the solution is set to 5.0 mm. With respect to the solution to which the reactive gas has been applied, a hydroxyl radical concentration is measured by electron spin resonance (ESR) method.

The radical concentration of the reactive gas transferred to the target surface by the plasma can be adjusted by the total distance of L1 and L2. The total distance of L1 and L2 is appropriately set in consideration of the desired size of the medical therapeutic apparatus 100, the temperature of the reactive gas at the target surface, and the like.

The total distance of L1 and L2 can be adjusted depending on the length of the outlet tube $1c$, and the installation positions of the inner electrode 4 and the outer electrode 5.

The radical concentration of the reactive gas transferred to the target surface by the plasma can be adjusted by the plasma gas temperature at the position of plasma generation.

The plasma gas temperature at the position of plasma generation is appropriately set depending on the level and frequency of the voltage applied between the inner electrode 4 and the outer electrode 5.

When the plasma gas temperature at the position of plasma generation is high, the radical concentration can be easily increased. When the plasma gas temperature at the position of plasma generation is low, the radical concentration can be easily decreased.

The singlet oxygen concentration of the reactive gas generated by the plasma is 0.1 to 300 µmol/L. The singlet oxygen concentration of the reactive gas generated by the plasma is preferably 0.1 to 100 µmol/L, more preferably 0.1 to 50 µmol/L.

When the singlet oxygen concentration of the reactive gas generated by the plasma is not lower than the lower limit value, the promotion of cleaning, activation or healing of abnormalities of a target object selected from a cell, a living tissue and a whole body of an organism is facilitated. When the singlet oxygen concentration is not more than the upper limit value, stimulus to the target surface can be easily reduced.

The singlet oxygen concentration of the reactive gas generated by the plasma can be determined by using the following singlet oxygen concentration measuring method using the medical therapeutic apparatus.

<Measuring Method of Singlet Oxygen Concentration>

A reactive gas is applied to 0.4 mL of a 0.1 mol/L solution of TPC (2,2,5,5-tetramethyl-3-pyrroline-3-carboxamide) for 30 seconds. Here, the distance from the outlet to a liquid surface of the solution is set to 5.0 mm. With respect to the solution to which the reactive gas has been applied, a singlet oxygen concentration is measured by electron spin resonance (ESR) method.

The singlet oxygen concentration of the reactive gas generated by the plasma can be adjusted by the flow rate of the plasma generating gas introduced into the tubular dielectric 3, the total distance of L1 and L2 and the plasma gas temperature at the position of plasma generation, some or all of which may be controlled in combination.

The adjustments of the flow rate of the plasma generating gas, the total distance of L1 and L2, and the plasma gas temperature are as mentioned above in connection with the radical concentration.

The reactive gas generated by the plasma preferably has a radical concentration of 0.1 to 300 µmol/L as well as a singlet oxygen concentration of 0.1 to 300 µmol/L.

When the concentrations of radical and singlet oxygen in the reactive gas generated by the plasma are within the ranges described above, the promotion of cleaning, activation or healing of abnormalities of a target object selected from a cell, a living tissue and a whole body of an organism is likely to be further facilitated.

The alternating voltage applied between the inner electrode 4 and the outer electrode 5 is preferably 5 kVpp or more and less than 20 kVpp. Here, the unit "Vpp (Volt peak to peak)" representing the alternating voltage means a potential difference between the highest value and the lowest value of the alternating voltage waveform.

When the inner electrode 4 is a cylindrical member having no irregularities on its outer peripheral surface, the alternating voltage applied between the inner electrode 4 and the outer electrode 5 is preferably 10 kVpp or more. When using the inner electrode 4 having no irregularities on its outer peripheral surface, the alternating voltage applied between the inner electrode 4 and the outer electrode 5 needs to be higher than in the case of using the inner electrode 4 having irregularities on its outer peripheral surface.

By setting the applied alternating voltage to less than the above upper limit value, the temperature of the generated plasma gas can be kept low. The plasma can be easily generated by setting the applied alternating voltage to not less than the above lower limit value.

The frequency of the alternating voltage applied between the inner electrode 4 and the outer electrode 5 is preferably 0.5 kHz or more and less than 20 kHz, more preferably 1 kHz or more and less than 15 kHz, even more preferably 2 kHz or more and less than 10 kHz, particularly preferably 3 kHz or more and less than 9 kHz, and most preferably from 4 kHz or more and less than 8 kHz.

With the frequency of the alternating voltage set to less than the above upper limit value, the temperature of the generated plasma can be suppressed low. With the frequency of the alternating voltage set to equal or exceed the above lower limit value, generation of plasma becomes easy.

The flow rate of the reactive gas blown out from the outlet 1a is preferably 1 L/min to 10 L/min.

When the flow rate of the reactive gas blown out from the outlet 1a is not less than the above lower limit value, efficiency for having the reactive gas act on the target surface can be sufficiently enhanced. When the flow rate of the reactive gas blown out from the outlet 1a is not more than the above upper limit value, excessive increase in the temperature of the reactive gas at the target surface can be prevented. In addition, when the target surface is wet, rapid drying of the target surface can be prevented. Furthermore, when the target surface is an affected part of a patient, pain inflicted on the patient due to heat can be further suppressed.

The type of the plasma generating gas to be introduced into the tubular dielectric 3 is not particularly limited, and for example, a known plasma generating gas such as oxygen, helium, argon, nitrogen, carbon dioxide, air or the like can be used.

As described above, the instrument 10 of the medical therapeutic apparatus 100 can generate and maintain plasma with low electric power as an effect achieved by the screw thread(s) provided on the outer peripheral surface of the inner electrode 4.

Therefore, in the present invention, not only the conventional noble gas but also a wide variety of plasma generating gases can be used.

The plasma generating gas to be introduced into the tubular dielectric 3 may be one type of gas or a mixture of two or more types of gasses.

The plasma generating gas introduced into the tubular dielectric 3 preferably contains nitrogen gas as a main component. Here, the nitrogen gas being contained as a main component means that the volume of the nitrogen gas contained in the plasma generating gas is more than 50% by volume. That is, the volume of the nitrogen gas contained in the plasma generating gas is preferably more than 50% by volume, more preferably 70% by volume or more, still more preferably 90 to 100% by volume. When the main component of the plasma generating gas is nitrogen gas, since the lifetime of metastable nitrogen molecules in the plasma is long, the activity of the gas is easily maintained, and the radical concentration of the reactive gas reaching the target object can be easily increased.

The type of the other gas components of the plasma generating gas is not particularly limited, and may be, for example, air. A mixed gas of air and nitrogen may be used as the plasma generating gas to generate a nitrogen gas plasma.

By using nitrogen as the main component, the plasma generating gas can further promote cleaning, activation or healing of the target object. In addition, by using nitrogen as a main component, the oxygen content of the plasma generating gas can be reduced and the ozone content of the reactive gas can be reduced. When the reactive gas application device 10 is used for treatment in the oral cavity, it is preferable to reduce the ozone content of the reactive gas.

With the conventional plasma generating unit, it is difficult to generate plasma with a plasma generating gas containing nitrogen. In the present embodiment, by the use of the inner electrode provided with a spiral ridge (screw thread) on the outer peripheral surface (namely, the inner electrode has a helical groove) is used, plasma can be easily generated.

The plasma generating gas to be introduced into the tubular dielectric 3 preferably has an oxygen concentration of 1% by volume or less. When the oxygen concentration is not more than the upper limit value, excessive generation of ozone can be further suppressed.

<<Method of Applying Reactive Gas>>

The reactive gas generated in the medical therapeutic apparatus 100 is preferably applied to living bodies such as cells, living tissues, whole bodies of organisms and the like. By applying the reactive gas to the living bodies, the living bodies can be treated or activated. For example, the application of the reactive gas to an affected part having trauma, such as cuts, scratches or burns, or other abnormalities, facilitates the inactivation of the bacteria on the surface suffering from the trauma or other abnormalities and produces an effect of promoting healing of the trauma and other abnormalities.

When applying the reactive gas to an affected part with trauma or other abnormalities, it may be required to reduce the dose of the gas for the purpose of suppressing stimulus to the patient. In such a case, by reducing the amount of the plasma generation gas introduced from the rear end of the tubular dielectric 3 of the medical therapeutic apparatus 100, the dose of the reactive gas blown out from the outlet 1a can be reduced.

In some cases, it may be required to further accelerate the healing by increasing the concentration of the reactive species contained in the reactive gas. In such cases, the application of the reactive gas may be performed while bringing the outlet 1a close to a target object such that the distance therebetween is 0.01 mm or more to 10 mm or less, which enables the application of an reactive gas containing a higher concentration of reactive species.

With the medical therapeutic apparatus 100, the temperature of the reactive gas to be applied can be set to 50° C. or less. Therefore, even when the outlet 1a is brought close to the target object, there is no risk of overheating the target object. Therefore, even when the application target is an affected part of a patient, it is possible to apply the reactive gas without giving an excessive stimulation to the affected part.

The reactive gas generated by the plasma generated in the medical therapeutic apparatus 100 have an effect of promoting healing of trauma and other abnormalities. As shown in the Examples to be described later, by applying a reactive gas generated by the plasma to cells, living tissues or whole bodies of organisms, the targeted part can be cleaned or activated, or the trauma or other abnormalities on the targeted part can be healed.

Examples of the living tissues include various organs such as internal organs, epithelial tissues covering the body surface and the inner surfaces of the body cavity, periodontal tissues such as gums, alveolar bone, periodontal ligament and cementum, teeth, bones and the like.

Examples of diseases and symptoms that can be treated by application of the reactive gas include diseases in the oral cavity such as gingivitis and periodontal disease, skin wounds and the like.

For applying a reactive gas generated by the plasma for the purpose of promoting healing of the trauma and other abnormalities, there is no particular limitation with regard to the interval, repetition number and duration of the application. For example, when the reactive gas generated by the plasma is applied to an affected part at a dose of 0.5 liter to 5.0 liter per minute, the frequency of daily application is preferably 1 to 5 times per day. With a dose of 0.5 liter to 5.0 liter per minute, the duration per one application is preferably 10 seconds to 10 minutes. With a dose of 0.5 liter to 5.0 liter per minute, the total duration for application is preferably 1 to 30 days. With these conditions, healing can be further promoted.

As described above, the medical therapeutic apparatus of the present embodiment can more stably generate a low-temperature plasma and apply the reactive gas generated by the plasma to the affected part. The applied reactive gas can promote tissue repair without damaging the targeted tissue. Therefore, the medical therapeutic apparatus of the present embodiment is also useful as a cosmetic instrument for skin, etc.

The medical therapeutic apparatus of the present invention is particularly useful as an oral cavity treatment apparatus and a dental treatment apparatus.

Further, the medical therapeutic apparatus of the present invention is also suitable as an animal treatment apparatus.

EXAMPLES

Hereinbelow, the present invention will be described with reference to Examples which, however, should not be construed as limiting the present invention.

(Temperature Measurement)

A medical therapeutic apparatus was produced, which is the same as the medical therapeutic apparatus 100 except for the specification of the apparatus as described below. Using the produced medical therapeutic apparatus, an alternating voltage of 15 kVpp, 7.5 kHz was applied between the outer electrode and the inner electrode to generate a nitrogen gas plasma with atmospheric pressure. In the room with a temperature of 25° C., a measuring part of thermocouple was positioned 3 mm away from the outlet. Blowing out of the reactive gas was initiated, and the temperature read 60 seconds after the initiation of the blowing out was taken as the temperature of the reactive gas at the target surface.

As a result, the temperature was 34.9° C. at a distance of 3 mm from the outlet.

<Specification>

Outlet 1a: inner diameter 1 mm.
Tubular dielectric 3: made of glass, inner diameter 3 mm.
Inner electrode 4: made of stainless steel, parallel-thread, single-threaded screw, outer diameter 2 mm, pitch 0.4 mm, thread height 0.214 mm.
Outer electrode 5: copper plate.
Angle θ: 20°.

(Measurement of Hydroxyl Radical Concentration)

Nitrogen gas having a purity of 99.99% (volume basis) was used as the plasma generating gas and introduced into the instrument at a flow rate of 1 L/min, and plasma was generated with an alternating voltage of 15 kVpp at 7.5 kHz. As the nozzle, one with an outlet having an inner diameter of 1 mm was used.

DMPO was used as a reagent for detecting hydroxyl radicals and dissolved in a phosphate-buffered physiological saline adjusted to pH 7.3 to 7.5 so that the DMPO concentration became 0.2 mol/L.

0.4 mL of the resulting DMPO solution was placed in a columnar cell having an inner diameter of 11.5 mm, and the instrument was installed such that the liquid surface of the solution in the cell was located 5 mm away from the outlet. A reactive gas generated by plasma was applied to the solution for 30 seconds, and the hydroxyl radical concentration of the solution after application of the reactive gas was measured by the ESR method. As a result, the radical concentration (hydroxyl radical concentration) was 3 µmol/L.

The conditions for the ESR method were as follows.

The frequency of the microwave was 9.63 GHz, and the microwave power was 10 mW. The above DMPO solution was placed in a magnetic field of 344±5 mT, and measurement was performed with a modulation amplitude of 0.2 mT and a sweep time of 20 seconds.

(Measurement of Singlet Oxygen Concentration)

The singlet oxygen concentration was measured in the same manner as in the measurement of hydroxyl radical concentration except that TPC was used as a reagent for detecting singlet oxygen and the concentration of TPC was 0.1 mol/L.

As a result, the singlet oxygen concentration was 3 µmol/L.

Promotion of Wound Healing, Examples 1 to 14, Comparative Examples 1 to 4

Back skins of 4 pigs were incised, cut out, and seeded with *Staphylococcus aureus* in the same area to prepare infected wound models. In accordance with the reactive gas generation conditions shown in Table 1, the reactive gas was applied to each of the infected wound models from a position as close to the model as possible. The application of the reactive gas was performed on the day of initiation of experiment (day 1) and day 7. The flow rate in Table 1 represents the flow rate of nitrogen gas introduced into the instrument. The voltage in Table 1 represents the alternating voltage applied between the inner electrode and the outer electrode. The frequency in Table 1 represents the frequency of the voltage applied between the inner electrode and the outer electrode. In Comparative Examples 1 to 4, no voltage was applied between the inner electrode and the outer electrode, which means that a nitrogen gas containing no reactive species was applied to the wound.

The clinical symptom score was determined by visually checking whether the wounds developed redness, erythema, papule, exudates (including pus) or pustule. The symptoms of the 5 items were scored based on the following criteria and totaled. The scores in Table 1 each represents an average value of the values determined for the 4 models (derived from 4 pigs) to which the reactive gas was applied under the same reactive gas generation conditions. The larger point indicates higher severity of the wound.

0 point: No wound
1 point: Minor
2 point: Moderate
3 point: Severe

The above clinical symptom scores were determined with respect to the wounds on the day on which the pigs were wounded (day 1) and the wounds on day 14, the score improvement rates (%) were calculated by the following formula.

Score improvement rate (%)=((clinical symptom score (day 1)−clinical symptom score (day 14))/clinical symptom score (day 1))×100

The results are shown in Table 1.

As shown in Table 1, in Examples 1 to 4 in which the flow rate of the reactive gas was set to 1 L/min, the score improvement rate was 76.9 to 84.4%, confirming wound healing effect of the reactive gas. In Examples 5 to 8 in which the flow rate of the reactive gas was set to 2 L/min, the score improvement rate was 89.2 to 93.6%, confirming higher wound healing effect of the reactive gas. In Examples 9 to 14 in which the flow rate of the reactive gas was 3 L/min, the score improvement rates were all 92.2% or more, confirming even higher wound healing effect of the reactive gas.

On the other hand, in Comparative Examples 1 to 4 (natural healing) in which nitrogen gas containing no reactive species was applied, the score improvement rate was 64.8% or less.

Photographs of the wounds in Examples 7, 8, 13 and 14 are shown in FIGS. 4 to 11. FIGS. 4, 6, 8 and 10 are

TABLE 1

| | Reactive gas generation conditions | | | | Clinical symptom scores | | |
| --- | --- | --- | --- | --- | --- | --- | --- |
| | Flow rate [L/min] | Voltage [kVpp] | Frequency [kHz] | Application time [sec] | Initial stage [Point] | Day 14 [Point] | Score improvement rate [%] |
| Ex. 1 | 1 | 10.5 | 7.5 | 15 | 12.8 | 2.5 | 80.5 |
| Ex. 2 | 1 | 10.5 | 7.5 | 30 | 12.8 | 2.0 | 84.4 |
| Ex. 3 | 1 | 10.5 | 7.5 | 60 | 13.0 | 3.0 | 76.9 |
| Ex. 4 | 1 | 10.5 | 7.5 | 120 | 12.8 | 2.8 | 78.1 |
| Ex. 5 | 2 | 10.5 | 7.5 | 15 | 13.0 | 1.0 | 92.3 |
| Ex. 6 | 2 | 10.5 | 7.5 | 30 | 12.5 | 0.8 | 93.6 |
| Ex. 7 | 2 | 15 | 7.5 | 15 | 13.0 | 1.0 | 92.3 |
| Ex. 8 | 2 | 15 | 7.5 | 30 | 13.0 | 1.4 | 89.2 |
| Ex. 9 | 3 | 10.5 | 7.5 | 15 | 12.8 | 1.0 | 92.2 |
| Ex. 10 | 3 | 10.5 | 7.5 | 30 | 13.0 | 0.5 | 96.2 |
| Ex. 11 | 3 | 10.5 | 7.5 | 60 | 12.8 | 1.0 | 92.2 |
| Ex. 12 | 3 | 10.5 | 7.5 | 120 | 12.8 | 1.0 | 92.2 |
| Ex. 13 | 3 | 15 | 7.5 | 15 | 13.3 | 0.7 | 94.7 |
| Ex. 14 | 3 | 15 | 7.5 | 30 | 13.3 | 0.3 | 97.7 |
| Comp. Ex. 1 | 1 | 0 | 0 | 30 | 12.8 | 5.8 | 54.7 |
| Comp. Ex. 2 | 2 | 0 | 0 | 30 | 12.8 | 4.5 | 64.8 |
| Comp. Ex. 3 | 3 | 0 | 0 | 30 | 13.0 | 6.0 | 53.8 |
| Comp. Ex. 4 | 3 | 0 | 0 | 60 | 12.5 | 4.5 | 64.0 | respectively photographs of the wounds before application of the reactive gas in Examples 7, 8, 13 and 14. FIGS. 5, 7, 9 and 11 are respectively photographs of the wounds on day 14 in Examples 7, 8, 13 and 14.

Figure 12:
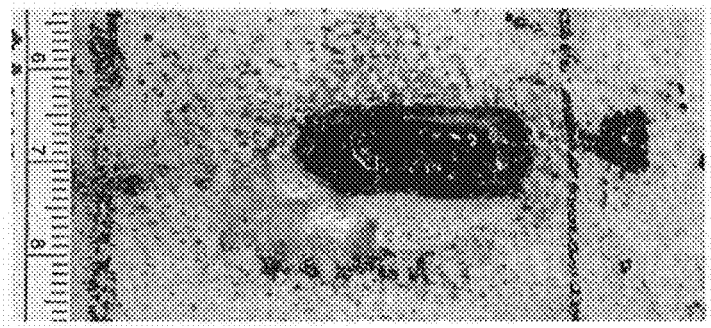
FIG. 12 is a photograph of an initial stage of the wound in Comparative Example 2.
Figure 13:
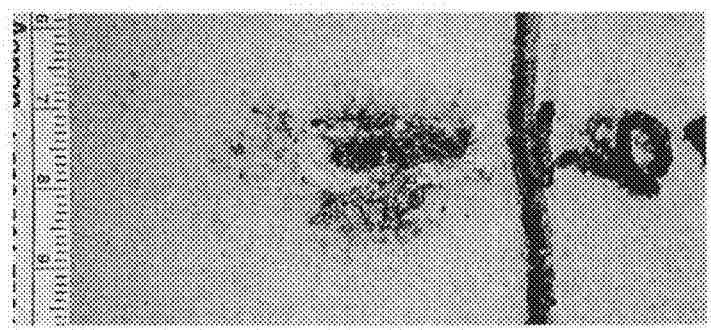
FIG. 13 is a photograph of the wound on day 14 in Comparative Example 2.
Figure 14:
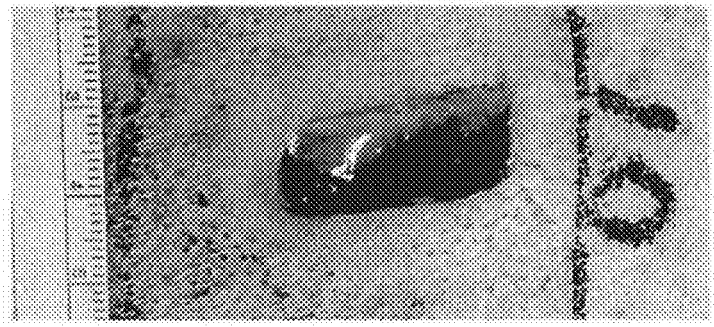
FIG. 14 is a photograph of an initial stage of the wound in Comparative Example 3.
Figure 15:
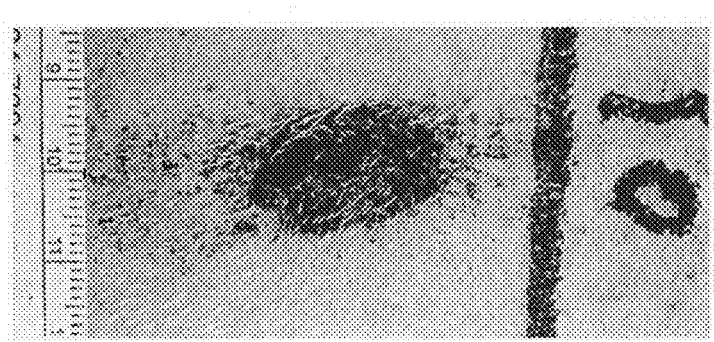
FIG. 15 is a photograph of the wound on day 14 in Comparative Example 3.

Photographs of the wounds in Comparative Examples 2 and 3 are shown in FIGS. 12 to 15. FIGS. 12 and 14 are photographs respectively showing initial stages of the wounds in Comparative Examples 2 and 3. FIGS. 13 and 15 are photographs respectively showing the wounds on day 14 in Comparative Examples 2 and 3.

From the comparison between FIGS. 5, 7, 9 and 11 showing the wounds on day 14 in Examples 7, 8, 13 and 14, and FIGS. 13 and 15 showing the wounds on day 14 in Comparative Examples 2 and 3, it is understood that the wound healing was better in the Examples.

Activation of Cells, Examples 10 to 12, Comparative Examples 1 and 4

For each of the wounds in Examples 10 to 12 and Comparative Examples 1 and 4, the pathological tissues on day 14 were collected and fixed with a 10% by mass neutral buffered formalin solution. The tissue cells in each of the Examples on day 14 day were observed with an optical microscope and photographed.

The results are shown in FIGS. 16 to 20. FIGS. 16 to 20 are photographs respectively taken in Examples 10 to 12 and Comparative Examples 1 and 4.

In FIGS. 16 to 20, the photographs on the right hand side are enlargements of framed sections in the photographs on the left hand side.

Figure 16:
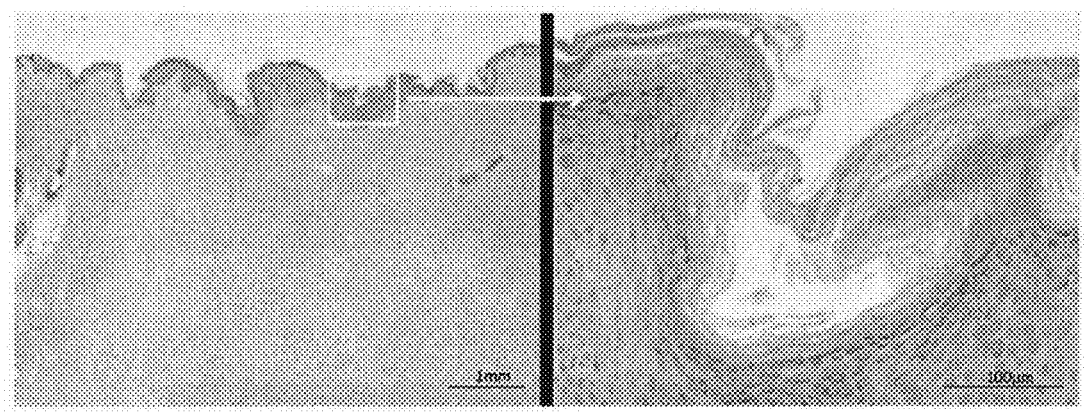
FIG. 16 is a photomicrograph of a tissue taken from the wound on day 14 in Example 10.
Figure 17:
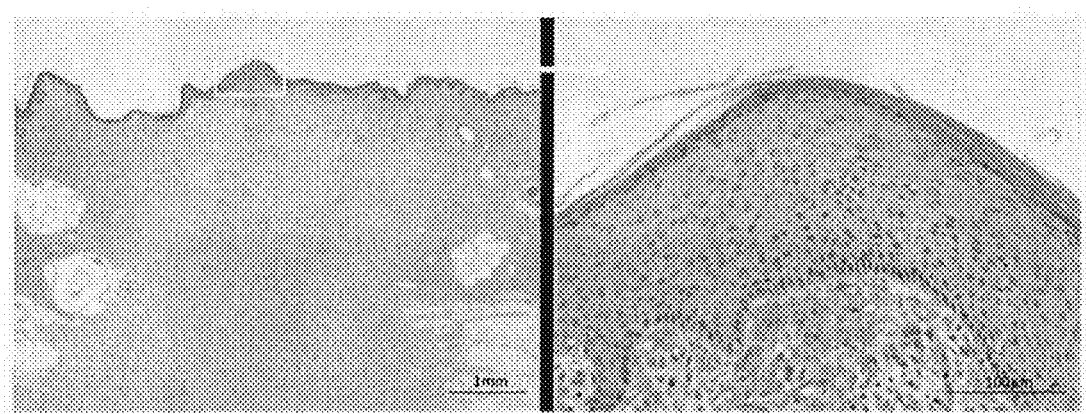
FIG. 17 is a photomicrograph of a tissue taken from the wound on day 14 in Example 11.
Figure 18:
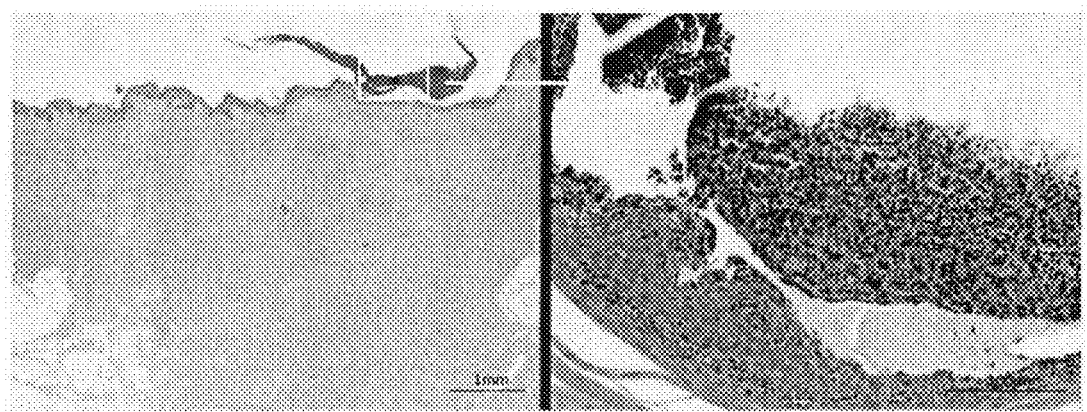
FIG. 18 is a photomicrograph of a tissue taken from the wound on day 14 in Example 12.

As shown in FIGS. 16 to 18, in Examples 10 to 12 in which the reactive gas was applied at a flow rate of 3 L/min, the epidermis was completely regenerated from the left and right of the wound site to construct an epidermal structure, and almost normal epidermis was regenerated, which confirmed the epidermal regeneration effect.

Infiltration of inflammatory cells, mainly lymphocytes, was observed at the wound site; however, fibroblasts had proliferated and the site of suppurative inflammation due to infiltration of neutrophils etc. has disappeared, so that the wound was considered to be in proliferative phase at middle to late stages of the wound healing process, which confirmed the wound healing and anti-inflammatory action.

Further, infected bacteria were not observed on the slices, and bactericidal action was observed.

Figure 19:
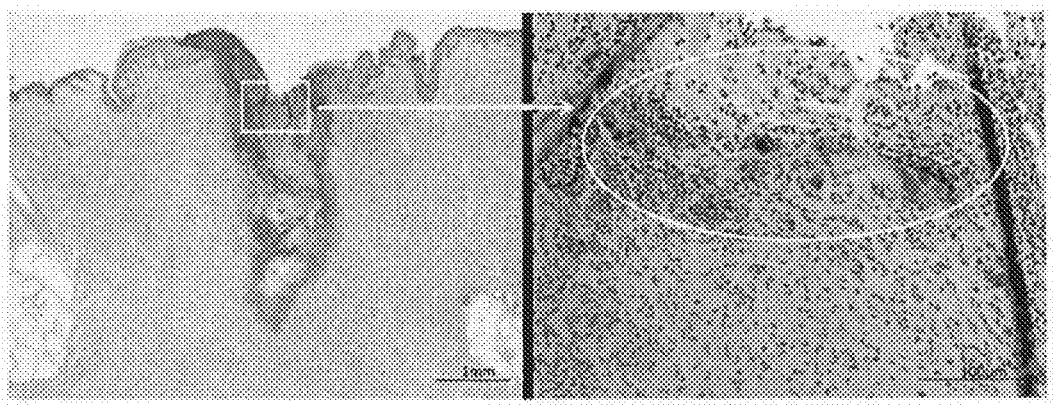
FIG. 19 is a photomicrograph of a tissue taken from the wound on day 14 in Comparative Example 1.
Figure 20:
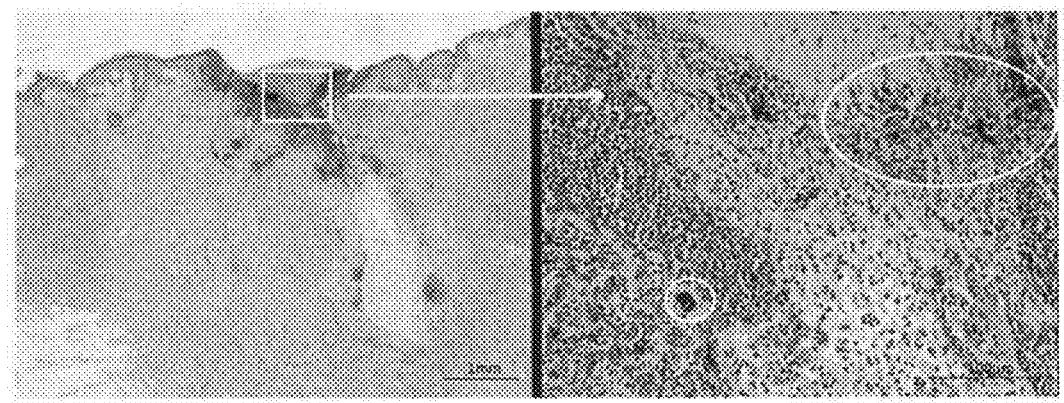
FIG. 20 is a photomicrograph of a tissue taken from the wound on day 14 in Comparative Example 4.

On the other hand, as shown in FIGS. 19 to 20, in Comparative Examples 1 and 4 (natural healing) in which nitrogen gas containing no reactive species was applied, the epidermis of the wound site diverged to the left and right, and the epidermal regeneration effect was not observed.

Furthermore, since the proportion of lymphocytes and neutrophils was large in the infiltrated inflammatory cells, while the proliferation of fibroblasts was relatively sparse and seemingly edematous image was observed locally, the wound was considered to be in inflammatory phase at early stage of wound healing process. Thus, the wound healing and anti-inflammatory action as observed in Examples 10 to 12 were not observed.

In addition, the infected bacteria survived, and no bactericidal action was observed.

INDUSTRIAL APPLICABILITY

The present invention is applicable in the medical field.

DESCRIPTION OF THE REFERENCE SIGNS

1 Nozzle
1a Outlet
1b Base
1c Outlet tube
2 Cowling
2a Head
2b Body
3 Tubular dielectric
4 Inner electrode
5 Outer electrode
6 to 8 Flow path
9 Switch
10 Instrument
20 Power supply unit
30 Gas conduit
40 Electric wiring
O1 to O2 Tube axis
100 Medical therapeutic apparatus

The invention claimed is:

1. A medical therapeutic apparatus which generates plasma and blows out a reactive gas generated by the generated plasma toward a target object from an outlet,
wherein a temperature of the reactive gas at a target surface positioned at a distance of 1 mm or more and 10 mm or less from the outlet is 40° C. or less, and at least one of the following requirements is satisfied: (1) a hydroxyl radical concentration is 0.1 to 300 μmol/L, and (2) a singlet oxygen concentration is 0.1 to 300 μmol/L,
wherein the hydroxy radical concentration is measured by a method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method, and
the singlet oxygen concentration is measured by a method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

2. The medical therapeutic apparatus according to claim 1, which is for dental use.

3. A method of using a medical therapeutic apparatus, comprising providing the medical therapeutic apparatus according to claim 2, and blowing out the reactive gas to a target object using the medical therapeutic apparatus.

4. A method of using a medical therapeutic apparatus, comprising providing the medical therapeutic apparatus according to claim 1, and blowing out the reactive gas to a target object using the medical therapeutic apparatus.

5. A method of applying an reactive gas to a target object, excluding medical practice on human body, comprising applying a voltage to a plasma generating gas to generate plasma, and applying a reactive gas generated by the plasma to a target object selected from a cell, a living tissue and a whole body of an organism, to thereby promote cleaning, activation or healing of abnormalities of the target object,
wherein a temperature of the reactive gas at a target surface positioned at a distance of 1 mm or more and 10 mm or less from the outlet is 40° C. or less, and at least one of the following requirements is satisfied: (1) a hydroxyl radical concentration is 0.1 to 300 μmol/L, and 12) a singlet oxygen concentration is 0.1 to 300 μmol/L, wherein the hydroxy radical concentration is measured by a method comprising applying the reactive gas to 0.4 mL of a 0.2 mol/L solution of DMPO (5,5-dimethyl-1-pyrroline-N-oxide) for 30 seconds with a distance from the outlet to a liquid surface of the solution being 5.0 mm, and measuring a hydroxyl radical concentration of the resulting solution by electron spin resonance (ESR) method, and the singlet oxygen concentration is measured by a method comprising applying the reactive gas to 0.4 mL of a 0.1 mol/L solution of TPC (2,2,5,5-tetramethyl-3-pyrroline-3-carboxamide) for 30 seconds with a distance from the outlet to a liquid surface of the solution being 5.0 mm, and measuring a singlet oxygen concentration of the resulting solution by electron spin resonance (ESR) method.

6. The method according to claim 5, wherein the plasma generating gas contains nitrogen gas as a main component.

7. The method according to claim 6, wherein the plasma generating gas has an oxygen concentration of 1% by volume or less.

8. The method according to claim 5, wherein the plasma generating gas has an oxygen concentration of 1% by volume or less.

* * * * *